United States Patent [19]

Kudschus

[11] Patent Number: 5,618,965

[45] Date of Patent: Apr. 8, 1997

[54] PROCESS FOR PREPARING AROMATIC NITRILES

[75] Inventor: Martin Kudschus, Givisiez, Switzerland

[73] Assignee: CIBA-GEIGY Corporation, Tarrytown, N.Y.

[21] Appl. No.: 610,315

[22] Filed: Mar. 4, 1996

[51] Int. Cl.$^6$ .................................................. C07C 253/00
[52] U.S. Cl. ........................... 558/315; 558/319; 558/346; 558/435; 558/55; 558/366
[58] Field of Search ...................................... 558/319, 315

[56] References Cited

U.S. PATENT DOCUMENTS 5,349,103  9/1994  Gülec .......................... 558/314

FOREIGN PATENT DOCUMENTS

| 0080700 | 4/1986 | European Pat. Off. . |
| 0144885 | 1/1987 | European Pat. Off. . |
| 0550762 | 7/1993 | European Pat. Off. . |
| 4407135 | 7/1995 | Germany . |

OTHER PUBLICATIONS

Chem. Abstract 114:101296d (1991).
J. Chem. Soc. IX, p. 43, (1933).
Chemistry & Industry 5, p. 176, (1991).
Synth. Comm. 22(14), pp. 2125–2128, (1992).
Synthesis, pp. 943–944, (1992).
Chem. Abstract 85:93176e of DD 117,872 (1976).
Chem. Abstract 90:151771m (1979).
Chem. Abstract 114:206700j (1991).

*Primary Examiner*—Johann Richter
*Assistant Examiner*—Ebenezer Sackey
*Attorney, Agent, or Firm*—Michele A. Kovaleski; George R. Dohmann

[57] ABSTRACT

Process for preparing a nitrile of the formula (I)

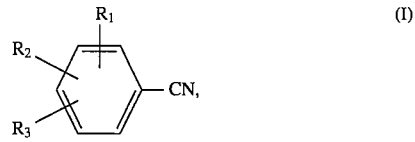

in which $R_1$, $R_2$ and $R_3$ are for example hydrogen, halogen, cyano, hydroxyl, carboxyl, alkyl, alkoxy, alkylthio, alkylamino, dialkylamino, aryl, aryloxy, arylthio or arylamino, or $R_2$ and $R_3$ together form a substituted or unsubstituted 4-membered carbon bridge, by reacting an aldehyde of the formula (II)

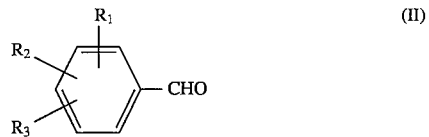

with a hydroxylammonium salt followed by dehydration by heating to an elevated temperature, wherein the reaction takes place in the presence of an anhydrous inorganic sulfate and in the absence of diluents from the group consisting of carboxylic acids, strongly polar aprotic solvents, sulfur compounds and heteroaromatic basic nitrogen compounds.

The nitriles obtainable by the process of the invention are valuable intermediates for, in particular, the preparation of diketopyrrolopyrrole pigments.

16 Claims, No Drawings

PROCESS FOR PREPARING AROMATIC NITRILES

The present invention relates to a process for preparing aromatic nitriles by solvent-free reaction of appropriate aldehydes with a hydroxylammonium salt and with an inorganic, anhydrous sulfate.

The reaction of aldehydes with hydroxylammonium salts and the subsequent dehydration of the resulting oxime to the nitrile have been known for a long time. A variety of methods have been proposed for the dehydration; for instance, C.A. 85, 93176e (1976) proposes heating in dimethylformamide, EP 080 700 proposes removal of the water by azeotropic distillation with the aid of a solvent which forms an azeotropic mixture and is immiscible with water, Synthesis 1979/2, 112–113 (1979) and Huaxue Shiji 12(5), 314, 292 (1990) propose heating in formic acid, Journal of Nanjing Univ., 26/2, 263–266 (1990), proposes heating in formic acid or glacial acetic acid, J. Chem. Soc. IX, 43 (1933) proposes heating in acetic anhydride, and EP 609179 proposes heating in propionic acid.

In EP 609179, in a reaction equation, it is postulated that, in the reaction of a benzaldehyde with hydroxylammonium sulfate and sodium propionate in propionic acid, sodium sulfate is formed, in which context it is critical that propionic acid is used as solvent. Moreover, this postulation contradicts the disclosed stoichiometry, which leads to sodium hydrogen sulfate.

However, the use of solvents on the industrial scale is nowadays avoided wherever possible for environmental and economic reasons, so that methods for the solvent-free preparation of nitriles are desirable. The preparation of oximes can be carried out without solvent by treating an aldehyde and hydroxylammonium chloride with microwaves in the presence of potassium fluoride adsorbed on alumina [Chemistry & Industry 1991/5, 176 (1991)], but the subsequent reaction to the nitrile requires the addition of carbon disulfide and acetonitrile. Nitriles can indeed be obtained, without a solvent, by treatment with microwaves or irradiation with infrared light, but in this case the reactants must be adsorbed on Mexican bentonite [Synthetic Communications 22/14, 2125–2128 (1992)].

It has been found that some of these known methods lead only to unsatisfactory yields, and that the purity of the benzonitriles prepared by the other known methods, especially in respect of the preparation of high-quality diketopyrrolopyrrole pigments, still leaves much to be desired. In particular, when the abovementioned bentonite method is applied to aldehydes, many of these aldehydes—apparently for reasons related to their structure—give very sparse yields.

It has now been found, quite surprisingly, that the same nitriles can be obtained in outstanding purity if a solvent is dispensed with and the reaction mixture comprising aldehyde and hydroxylammonium salt is simply heated together with an anhydrous inorganic sulfate. Unexpectedly, the yield is about the same as with the use of propionic acid as solvent (EP 609179) and, very surprisingly, is much higher than with the use of a clay under solvent-free conditions. Because of this, a further advantage is the possibility of a higher volume yield.

This is all the more astonishing since the anhydrous inorganic sulfates which mark out the present invention do not give an acid reaction, do not have an active surface and do not exhibit any particular adsorption capacity for organic molecules.

The decisive factor for the surprisingly good results of the present invention is that, under these conditions, it is possible to achieve a precisely controlled reaction and shorter reaction times. The choice of favourable, different temperatures for the reaction to give the oxime and, respectively, for the subsequent dehydration to the nitrile promotes rapid and highly selective reactions, so that the formation of by-products, and in particular the formation of the unwanted carboxamide, is largely prevented.

The present invention provides, accordingly, a process for preparing a nitrile of the formula (I)

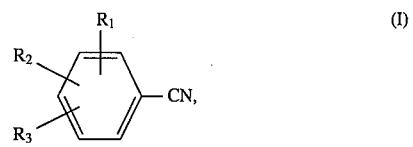

in which $R_1$, $R_2$ and $R_3$ independently of one another are hydrogen, halogen, cyano, hydroxyl, carboxyl, $C_1$–$C_{18}$alkyl, $C_1$–$C_{18}$alkoxy, $C_1$–$C_{18}$alkylthio, $C_1$–$C_{18}$alkylsulfonyl, $C_1$–$C_{18}$alkylamino, di($C_1$–$C_{18}$alkyl)amino, $R_4$–$C_6$–$C_{10}$aryl, $R_4$–$C_6$–$C_{10}$aryloxy, $R_4$–$C_6$–$C_{10}$arylthio, $R_4$–$C_6$–$C_{10}$arylsulfonyl or $R_4$–$C_6$–$C_{10}$arylamino.

or, where $R_2$ and $R_3$ are ortho to one another, $R_2$ and $R_3$ together form a saturated or mono- or di-unsaturated, 4-membered carbon bridge which is substituted with a radical $R_4$, and $R_4$ is hydrogen, halogen, cyano, hydroxyl, carboxyl, $C_1$–$C_{18}$alkyl, $C_1$–$C_{18}$alkoxy, $C_1$–$C_{18}$-alkylthio, $C_1$–$C_{18}$alkylsulfonyl, $C_1$–$C_{18}$alkylamino or di($C_1$–$C_{18}$alkyl)amino, by reacting an aldehyde of the formula (II)

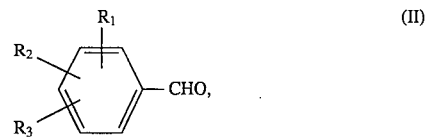

in which $R_1$, $R_2$ and $R_3$ are as defined above, with a hydroxylammonium salt followed by dehydration by heating to an elevated temperature, wherein the reaction takes place in the presence of an anhydrous inorganic sulfate and in the absence of diluents from the group consisting of carboxylic acids, strongly polar aprotic solvents, sulfur compounds and heteroaromatic basic nitrogen compounds.

Advantageous anhydrous inorganic sulfates are those which give stable bisulfates on acidification. Examples which can be used are sodium sulfate, potassium sulfate, lithium sulfate or ammonium sulfate, with sodium sulfate being preferred.

The hydroxylammonium salt is, for example, hydroxylammonium chloride or hydroxylammonium sulfate, preferably hydroxylammonium sulfate.

Halogen is for example chlorine, bromine or fluorine.

$C_1$–$C_8$alkyl, itself or as a part of $C_1$–$C_8$alkyl, $C_1$–$C_{18}$-alkoxy, $C_1$–$C_{18}$-alkylthio, $C_1$–$C_{18}$alkylsulfonyl, $C_1$–$C_{18}$alkylamino or di($C_1$–$C_{18}$alkyl)amino, is, for example, $C_1$–$C_4$alkyl, such as methyl, ethyl, n-propyl, isopropyl, n-butyl, sec-butyl, tert-butyl or isobutyl, or n-pentyl, n-hexyl, n-octyl, 2,2-dimethylpropyl or 1,1,3,3-tetramethylbutyl.

$C_6$–$C_{10}$aryl, itself or as part of $R_4$–$C_6$–$C_{10}$aryl, $R_4$–$C_6$–$C_{10}$aryloxy, $R_4$–$C_6$–$C_{10}$arylthio, $R_4$–$C_6$–$C_{10}$arylsulfonyl or $R_4$–$C_6$–$C_{10}$arylamino, is phenyl or naphthyl.

Since in the present process the organic constituents should advantageously be in liquid form, it is possible to use aromatic aldehydes having a melting point ≦125° C. to prepare aromatic nitriles having a melting point ≦170° C.

and a boiling point ≦170° C./1 mbar entirely in the absence of solvent.

However, it is also possible to add inert diluents, with the exception of carboxylic acids, heteroaromatic basic nitrogen compounds, sulfur compounds and strongly polar compounds, in relatively small quantities. By this means it is possible, for example, to improve the viscosity or the distribution, to promote the melting of the initial aldehyde or to prevent the precipitation of the nitrile which forms, so that the desired reactions to give the oxime and/or the nitrile are favoured.

The inert diluents may be high-boiling liquids or solids with a melting point ≦70° C. which are of low polarity (dipole moment $\mu \leq 2 \times 10^{-18}$ esu), for example hydrocarbons, ethers, alcohols or mixtures thereof, such as petroleum fractions, petroleum, low-melting waxes, Shell-Sol®, Solvesso®, Dowtherm®, trichlorobenzene, diethylene glycol dimethyl ether, n-octanol or ethyl benzoate, which have a boiling point ≧150° C./ 1 bar, preferably a boiling point ≧150° C./5 mbar.

Diluents regarded as inert are those which remain completely unchanged during the reaction, or whose follow-on products lead at most to traces of impurities in the end product (i.e. ≦1% by weight, based on the nitrile).

Carboxylic acids, heteroaromatic basic nitrogen compounds, sulfur compounds and strongly polar compounds (dipole moment $\mu > 2 \times 10^{-18}$ esu), for example propionic acid, acetic acid, formic acid, pyridine, quinoline, carbon disulfide, dimethyl sulfoxide and dimethylformamide, exert an unwanted influence on the course of the reaction, or hamper the working-up procedure, and are therefore unsuitable as diluents.

The aldehydes of the formula (II) are known compounds, for example benzaldehyde, 2-, 3- or 4-chlorobenzaldehyde, 2- or 3-methoxybenzaldehyde, anisaldehyde, 2-, 3- or 4-tolualdehyde, 4-tert-butylbenzaldehyde, biphenyl-4-carbaldehyde, mesitylene-2-carbaldehyde, 1- or 2-naphthaldehyde, 3- or 4-phenoxybenzaldehyde or tetralin-2-carbaldehyde. Should certain aldehydes of the formula (II) not be known compounds, they can be prepared by known methods.

Preference is given to the preparation of aromatic nitriles of the formula (I) having a boiling point ≦170° C./1 mbar from aldehydes of the formula (II) having a melting point ≦125° C.

Preference is likewise given to the preparation of aromatic nitriles of the formula (I), in which $R_1$, $R_2$ and $R_3$ independently of one another are hydrogen, halogen, cyano, hydroxyl, carboxyl, $C_1$–$C_8$alkyl, $C_1$–$C_8$alkoxy, $C_1$–$C_8$alkylthio, $C_1$–$C_8$alkylamino, di($C_1$–$C_8$alkyl)amino, $R_4$-$C_6$–$C_{10}$aryl, $R_4$-$C_6$–$C_{10}$aryloxy, $R_4$-$C_6$–$C_{10}$arylthio or $R_4$-$C_6$–$C_{10}$arylamino, or, where $R_2$ and $R_3$ are ortho to one another, $R_2$ and $R_3$ together form a saturated or mono- or di-unsaturated, 4-membered carbon bridge which is substituted with a radical $R_4$, and $R_4$ is hydrogen, halogen, cyano, hydroxyl, carboxyl, $C_1$–$C_8$alkyl, $C_1$–$C_8$alkoxy, $C_1$–$C_8$alkylthio, $C_1$–$C_8$alkylamino or di($C_1$–$C_8$alkyl)amino.

Particular preference is given to the preparation of aromatic nitriles of the formula (I), in which $R_1$, $R_2$ and $R_3$ independently of one another are hydrogen, halogen, $C_1$–$C_4$alkyl, $C_1$–$C_4$alkoxy, di($C_1$–$C_4$alkyl)amino, $R_4$-$C_6$–$C_{10}$aryl, $R_4$-$C_{6l}$ –$C_{10}$aryloxy or $R_4$-di($C_6$–$C_{10}$aryl)amino, and $R_4$ is hydrogen, halogen, $C_1$–$C_2$alkyl, $C_1$–$C_2$alkoxy or di($C_1$–$C_2$alkyl)amino, especially to the preparation of aromatic nitriles of the formula (I), in which $R_1$ is hydrogen, chlorine, methyl, methoxy, tert-butyl or phenyl, very preferably 4-methyl, 4-tert-butyl or 4-phenyl, especially 4-phenyl, $R_2$ and $R_3$ either are each hydrogen or both together are ω-buta-1,3-dienylene, and $R_4$ is hydrogen.

The hydroxylammonium salt is preferably employed in an at least stoichiometric quantity, and particularly preferably with a slight excess, i.e. from 0.505 to 0.58 mol of $(NH_2OH)_2 \cdot H_2SO_4$ per mole of aldehyde.

The anhydrous sulfate is expediently employed in a quantity of from 1 to 20 mol, preferably from 2 to 12 mol, per mole of aldehyde.

A preferred embodiment of the invention, which astonishingly gives rise to high yields which can be obtained with particularly good reproducibility, uses an anhydrous sulfate whose fractions having a particle size ≦50 μm constitute at least 1% by weight of the overall quantity of anhydrous sulfate. It is particularly preferred for the anhydrous sulfate to contain from 2 to 20% by weight, very preferably from 5 to 15 % by weight and, in particular, about 10% by weight of fractions having a particle size ≦50 μm. The fraction with a particle size ≦50 μm can be determined by sieving the anhydrous sulfate through a 50 μm sieve.

Anhydrous sulfate containing 10% by weight of fractions having a particle size ≦50 μm can be prepared, for example, by forming an intimate mixture from 90 parts by weight of a relatively coarse anhydrous sulfate (for example the sieve residue in the 50 μm sieve), with 10 parts by weight of a relatively fine anhydrous sulfate (which has been, for example, ground and sieved through a 50 μm sieve).

Diluents are added if desired in quantities of up to 150% by weight, preferably up to 50% by weight, based on the aldehyde employed.

The optimum temperature programme for the heating of the reaction mixture depends on the respective aldehyde. It is advantageous to carry out heating in two stages, over the course of 1–5 hours, from 25° C. initially to 50°–120° C., and then to 100°–200° C.; in this case, what happens at the first temperature is primarily that the oxime is formed and the sulfuric acid from the sulfate is bound, while at the second, higher temperature the nitrile is formed completely and the water of reaction formed is removed by distillation.

Preference is given to reaction times at the second, higher temperature which are as short as possible. It is therefore advantageous to carry out the reaction under reduced pressure, preferably at 2–100 mbar, particularly preferably at 5–50 mbar, at which the water of reaction formed can be removed with particular rapidity by distillation.

Working up can be carded out, for example, conventionally, by separating the crude product from the insoluble salt, with or without the aid of an organic solvent, or by dissolving the inorganic constituents in water and separating off the aqueous phase. The pure product can subsequently be obtained from the crude product by, for example, crystallization, distillation or any other of the wide range of methods familiar to the person skilled in the art.

Where working up is carried out conventionally, it is preferred to use an inert organic solvent having a low boiling point (-40°–120° C.), such as acetone, methyl ethyl ketone, methanol, ethyl acetate or toluene. Preference is given to toluene and, in particular, to methanol.

The preferred working-up procedure, however, is the direct distillation of the pure product from the reaction mixture directly after the end of dehydration, by increasing the temperature and/or reducing the pressure. In this way it is possible to obtain nitriles in particularly high purity.

Where working up is carried out by a distillative method, it is possible by choosing appropriate distillation conditions to increase still further the degree of purity of the pure product, by selecting, for example, a distillation column having a plurality of theoretical plates and a high reflux ratio at the top. The person skilled in the art is very familiar with the establishment of the desired quality by exerting influence on the distillation parameters.

In general, however, it is unnecessary to take special measures in the distillation of the product, since the purity of the products prepared by the present invention is, surprisingly, already extremely high.

Where the distillation produces mixed fractions essentially comprising aldehyde and nitrile, then, in proportion to the fraction of the aldehyde they contain, these mixed fractions can advantageously be reused as starting material for the process according to the invention. The possibility of recycling the unreacted aldehyde is therefore a further advantage of the process of the invention.

The nitriles obtainable by the process according to the invention are valuable intermediates for, inter alia, the preparation of 1,4-diketo-2,5-dihydro-3,6-diarylpyrrolo[4,3-c]pyrrole pigments, for which the high purity of the nitriles makes them particularly suitable. The preparation of diketopyrrolopyrrole pigments starting from nitriles is well known and is described, for example, in U.S. Pat. No. 4,579,949.

The examples which follow illustrate the invention:

EXAMPLE 1

With stirring (20 rpm), a turbine dryer is charged at room temperature with 1007 parts by weight of anhydrous sodium sulfate, 222 parts by weight of biphenyl-4-carbaldehyde and 105 parts by weight of hydroxylammonium sulfate. Following evacuation to 13 mbar, the mixture is heated to 70° C. and stirred at this temperature for 3 hours. It is subsequently heated at 130° C., during which about 43 parts by weight of water are removed by distillation. After half an hour, the pressure is reduced to 4 mbar and the jacket temperature is raised successively to 170° C. over the course of 60–70 minutes, the product undergoing fractional distillation. 194 parts by weight of biphenyl-4-carbonitrile are obtained with an outstanding purity of ~98–99% (HPLC) and a melting point of 83°–85° C., along with 10 parts by weight of a less pure fraction.

EXAMPLE 2

With stirring (20 rpm), a turbine dryer is charged at room temperature with 1800 parts by weight of anhydrous sodium sulfate, 365 parts by weight of 4-tert-butylbenzaldehyde and 194 parts by weight of hydroxylammonium sulfate. Following evacuation to 25 mbar, the mixture is heated to 100° C. and stirred at this temperature for 2 hours. It is subsequently heated at 125° C. for 40 minutes, during which about 82 parts by weight of water are removed by distillation. The distillation of the nitrile is then initiated and controlled by successive reduction of the pressure to 10 mbar and raising of the jacket temperature to 170° C. 300 parts by weight of 4-tert-butylbenzonitrile are obtained with an outstanding purity of ~98–99% (HPLC), along with 18 parts by weight of a less pure fraction.

EXAMPLE 3

With stirring (20 rpm), a turbine dryer is charged at room temperature with 8000 parts by weight of anhydrous sodium sulfate, 1602 parts by weight of 4-methylbenzaldehyde and 1149 parts by weight of hydroxylammonium sulfate. Following evacuation to 35 mbar, the mixture is heated to 80° C. and stirred at this temperature for 2½ hours. It is subsequently heated at 125° C. at a pressure of 80 mbar and held for 10 minutes; the pressure is then reduced to 60 mbar and held for a further 20 minutes, during which a total of about 480 parts by weight of water are removed by distillation. The distillation of the nitrile is initiated and controlled by successive reduction of the pressure to 10 mbar and subsequent raising of the jacket temperature to 170° C. 1265 parts by weight of 4-methylbenzonitrile are obtained with a purity of over 98% (HPLC), and also 37 parts by weight of a mixed fraction essentially consisting of 4-methylbenzonitrile and 4-methylbenzaldehyde.

EXAMPLE 4

With stirring (20 rpm), a turbine dryer is charged at room temperature with 4000 parts by weight of anhydrous sodium sulfate, 951 parts by weight of vanillin and 538.6 parts by weight of hydroxylammonium sulfate. Following evacuation to 10 mbar, the mixture is heated to 85° C. and stirred at this temperature for 3 hours. It is subsequently heated at 130° C. and held for 25 minutes at the same pressure. A total of about 250 parts by weight of water are removed by distillation altogether. The distillation of the nitrile is initiated and controlled by reduction of the pressure to 5 mbar and subsequent raising of the jacket temperature to 200° C. 693 parts by weight of vanillic acid nitrile are obtained with a purity of over 98% (TLC) and a melting point of 87.5°–89.5° C., and also 43.5 parts by weight of a mixed fraction essentially consisting of vanillic acid nitrile and vanillin.

EXAMPLE 5

With stirring (20 rpm), a turbine dryer is charged at room temperature with 4000 parts by weight of anhydrous sodium sulfate, 951 parts by weight of vanillin and 538.6 parts by weight of hydroxylammonium sulfate. Following evacuation to 10 mbar, the mixture is heated to 85° C. and stirred at this temperature for 3 hours. It is subsequently heated at 130° C. and held for 25 minutes at the same pressure. A total of about 250 parts by weight of water are removed by distillation altogether. The reaction mixture is then cooled to 100° C. and nitrogen is introduced until atmospheric pressure is reached. After 3000 parts by weight of toluene are added, the mixture is kept for 20 min at 100° C., then cooled down to room temperature while further stirred. The suspension is filtered, and the filter cake is extracted three times each with 3000 parts by weight of hot toluene. The solvent extracts are combined with the first filtrate and evaporated to dryness. The residue (about 875 parts by weight) is dissolved in 5500 parts by weight of dichloromethane and subjected to column chromatography using 2100 parts by weight of silica gel 60 [70–230 mesh (Merck)] and 33000 parts by weight of dichloromethane as eluent. After a portion corresponding to the dead volume of the column is first discarded, the next 30000 parts by weight are collected in one fraction and evaporated to dryness. 719 parts by weight of vanillic acid nitrile are obtained with a purity of over 98% (TLC) and a melting point of 88°–90° C.

EXAMPLE 6

With stirring (20 rpm), a turbine dryer is charged at room temperature with 4000 parts by weight of anhydrous sodium sulfate, 950 parts by weight of 4-(methylthio)benzaldehyde and 538.4 parts by weight of hydroxylammonium sulfate.

Following evacuation to 25 mbar, the mixture is heated to 80° C. and stirred at this temperature for 3 hours. It is subsequently heated at 130° C. and held for 30 minutes at the same pressure. A total of about 240 parts by weight of water are removed by distillation altogether. The distillation of the nitrile is initiated and controlled by reduction of the pressure to 5 mbar and subsequent raising of the jacket temperature to 150° C. 708 parts by weight of 4-(methylthio)benzonitrile are obtained with a purity of over 98% (TLC), and also 18 parts by weight of a mixed fraction essentially consisting of 4-(methylthio)benzonitrile and 4-(methylthio)benzaldehyde. The collected 4-(methylthio)benzonitrile has a melting point of 61°–63° C.

EXAMPLE 7

With stirring (20 rpm), a turbine dryer is charged at room temperature with 1280 parts by weight of anhydrous sodium sulfate, 462 parts by weight of 3-bromo-4-hydroxy-5-methoxybenzaldehyde, 172 parts by weight of hydroxylammonium sulfate and 298 parts by weight of 1-chloronaphthalin. Following evacuation to 70 mbar, the mixture is heated to 130° C. and kept at this temperature for 3½ hours. The reaction mixture is then cooled to 30° C. and nitrogen is introduced until atmospheric pressure is reached. After 2650 parts by weight of dichloromethane are added, the suspension is kept for 20 min at room temperature while further stirred and then filtered. The filter cake is extracted three times each with 2000 parts by weight of dichloromethane. The solvent extracts are combined with the first filtrate and evaporated to ⅓ of their volume. The solution of the raw product in dichloromethane is subjected to column chromatography using 1400 parts by weight of silica gel 60 [70–230 mesh (Merck)] and 26500 parts by weight of dichloromethane as eluent. After a portion corresponding to the dead volume of the column is first discarded, the next 17000 parts by weight are collected in one fraction and evaporated to dryness. The residue is freed from traces of adsorbed 1-chloronaphthalin at 80° C. in the vacuum. 334.5 parts by weight of 3-bromo-4-hydroxy-5-methoxybenzonitrile are obtained with a purity of over 98% (TLC) and a melting point of 144°–145° C.

EXAMPLE 8

With stirring (20 rpm), a turbine dryer is charged at room temperature with 1280 parts by weight of anhydrous sodium sulfate, 462 parts by weight of 3-bromo-4-hydroxy-5-methoxybenzaldehyde and 172 parts by weight of hydroxylammonium sulfate. Following evacuation to 25 mbar, the mixture is heated to 130° C. and kept at this temperature for 3½ hours. The reaction mixture is then cooled to 30° C. and nitrogen is introduced until atmospheric pressure is reached. After 2650 parts by weight of dichloromethane are added, the suspension is kept for 20 min at room temperature while further stirred and then filtered. The filter cake is extracted three times each with 2000 parts by weight of dichloromethane. The solvent extracts are combined with the first filtrate and evaporated to ⅓ of their volume. The solution of the raw product in dichloromethane is subjected to column chromatography using 1400 parts by weight of silica gel 60 [70–230 mesh (Merck)] and 26500 parts by weight of dichloromethane as eluent. After a portion corresponding to the dead volume of the column is first discarded, the next 17000 parts by weight are collected in one fraction and evaporated to dryness. The residue is dried at 80° C.

281 parts by weight of 3-bromo-4-hydroxy-5-methoxybenzonitrile are obtained with a purity of over 95% (TLC/rest=3-bromo-4-hydroxy-5-methoxybenzaldehyde) and a melting point of 139°–142° C.

What is claimed is:

1. A process for preparing a nitrile of the formula (I)

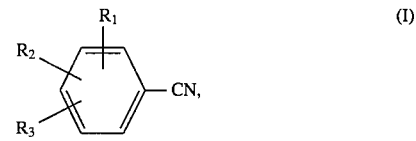

in which $R_1$, $R_2$ and $R_3$ independently of one another are hydrogen, halogen, cyano, hydroxyl, carboxyl, $C_1$–$C_{18}$alkyl, $C_1$–$C_{18}$alkoxy, $C_1$–$C_{18}$alkylthio, $C_1$–$C_{18}$alkylsulfonyl, $C_1$–$C_{18}$alkylamino, di($C_1$–$C_{18}$-alkyl)amino, $R_4$–$C_6$–$C_{10}$aryl, $R_4$–$C_6$–$C_{10}$aryloxy, $R_4$–$C_6$–$C_{10}$arylthio, $R_4$–$C_6$–$C_{10}$ arylsulfonyl or $R_4$–$C_6$–$C_{10}$arylamino, or, where $R_2$ and $R_3$ are ortho to one another, $R_2$ and $R_3$ together form a saturated or mono- or di-unsaturated, 4-membered carbon bridge which is substituted with a radical $R_4$, and $R_4$ is hydrogen, halogen, cyano, hydroxyl, carboxyl, $C_1$–$C_{18}$alkyl, $C_1$–$C_{18}$alkoxy, $C_1$–$C_{18}$alkylthio, $C_1$–$C_{18}$alkylsulfonyl, $C_1$–$C_{18}$alkylamino or di($C_1$–$C_{18}$alkyl)amino, by reacting an aldehyde of the formula (II)

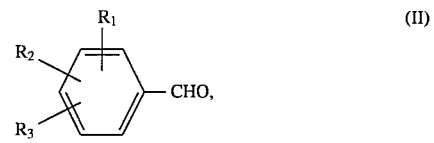

in which $R_1$, $R_2$ and $R_3$ are as defined above, with a hydroxylammonium salt followed by dehydration by heating to an elevated temperature, wherein the reaction takes place in the presence of an anhydrous inorganic sulfate and in the absence of diluents from the group consisting of carboxylic acids, strongly polar aprotic solvents, sulfur compounds and heteroaromatic basic nitrogen compounds.

2. A process according to claim 1, wherein anhydrous sodium sulfate, potassium sulfate, lithium sulfate or ammonium sulfate is used.

3. A process according to claim 1, wherein anhydrous sodium sulfate is used.

4. A process according to claim 1, wherein hydroxylammonium sulfate is used.

5. A process according to claim 1, wherein an anhydrous inorganic sulfate is used whose fractions having a particle size $\leq 50$ μm constitute at least 1% by weight of the overall quantity of anhydrous sulfate.

6. A process according to claim 5, wherein the anhydrous inorganic sulfate contains from 2 to 20% by weight of fractions having a particle size $\leq 50$ μm.

7. A process according to claim 6, wherein the anhydrous inorganic sulfate contains from 5 to 15% by weight of fractions having a particle size $\leq 50$ μm.

8. A process according to claim 1, wherein in addition an inert diluent having a melting point $\leq 70°$ C., a boiling point $\geq 150°$ C./1 bar and dipole moment $\mu \leq 2 \times 10^{-18}$ esu, with the exception of carboxylic acids, heteroaromatic basic nitrogen compounds, sulfur compounds and strongly polar compounds, is added if desired in quantities of up to 150% by weight, based on the aldehyde employed.

9. A process according to claim 1, wherein $R_1$, $R_2$ and $R_3$ independently of one another are hydrogen, halogen, $C_1$–$C_4$alkyl, $C_1$–$C_4$alkoxy, di($C_1$–$C_4$alkyl)amino, $R_4$-$C_6$–$C_{10}$aryl, $R_4$-$C_6$–$C_{10}$aryloxy or $R_4$-di($C_6$–$C_{10}$aryl)amino, and $R_4$ is hydrogen, halogen, $C_1$–$C_2$alkyl, $C_1$–$C_2$alkoxy or di($C_1$–$C_2$alkyl)amino.

10. A process according to claim 1, wherein $R_1$ is hydrogen, chlorine, methyl, methoxy, tert-butyl or phenyl, $R_2$ and $R_3$ either are each hydrogen, or both together are ω-buta-1,3-dienylene, and $R_4$ is hydrogen.

11. A process according to claim 10, wherein $R_1$ is 4-methyl, 4-tert-butyl or 4-phenyl.

12. A process according to claim 11, wherein $R_1$ is 4-phenyl.

13. A process according to claim 1, wherein the hydroxylammonium salt is employed in quantities of from 0.505 to 0.58 mol, and the anhydrous sulfate in quantities of from 2 to 12 mol, in each case per mole of aldehyde.

14. A process according to claim 1, in which the nitrile of the formula (I) is subsequently isolated from the reaction mixture by direct distillation.

15. A process of claim 8 wherein up to 50% by weight of the inert diluent is added.

16. A process of claim 1 wherein the nitrile of formula (I) is subsequently converted to a 1,4-diketo-2,5-dihydro-3,6diarylpyrrolo[4,3-c]pyrrole pigment.

* * * * *